US012724941B2

(12) United States Patent
Pereira Dos Santos et al.

(10) Patent No.: US 12,724,941 B2
(45) Date of Patent: Sep. 1, 2026

(54) METHOD FOR DETERMINING THE CONTENT, QUALITY AND MATURATION OF ORGANIC MATTER IN MARINE ENVIRONMENT FOR EXPLORATION OF OIL WELLS

(71) Applicants: Petróleo Brasileiro S.A.—Petrobras, Rio de Janeiro (BR); Universidade Federal Fluminense—UFF, Niterói (BR)

(72) Inventors: Thiago Pereira Dos Santos, Niterói (BR); Rut Amelia Díaz Ramos, Niterói (BR); Pedro Vitor Abreu Affonso, Niterói (BR); Marcelo Corréa Bernardes, Niterói (BR); Manuel Antonio Moreira Ramirez, Niterói (BR); Lucas Lopes Do Couto, Niterói (BR); Igor Viegas Alves Fernandes De Souza, Rio de Janeiro (BR); Igor Martins Venancio Padilha De Oliveira, Niterói (BR); Fellippe Roberto Alves Bione De Araújo, Niterói (BR); Andre Luiz Durante Spigolon, Rio de Janeiro (BR); Andre Luiz Belem, Niterói (BR); Ana Luiza Spadano Albuquerque, Niterói (BR)

(73) Assignees: Petróleo Brasileiro S.A.—Petrobras, Rio de Janeiro (BR); Universidade Federal Fluminense—UFF, Niteroi (BR)

( * ) Notice: Subject to any disclaimer, the term of this patent is extended or adjusted under 35 U.S.C. 154(b) by 896 days.

(21) Appl. No.: 18/083,972

(22) Filed: Dec. 19, 2022

(65) Prior Publication Data

US 2023/0195966 A1 Jun. 22, 2023

(30) Foreign Application Priority Data

Dec. 18, 2021 (BR) ...................... 10 2021 025711 3

(51) Int. Cl.
*G06F 30/20* (2020.01)
*G01N 33/24* (2006.01)
*G06F 113/08* (2020.01)

(52) U.S. Cl.
CPC ............. *G06F 30/20* (2020.01); *G01N 33/24* (2013.01); *G06F 2113/08* (2020.01)

(58) Field of Classification Search
CPC ...... G06F 30/20; G06F 2113/08; G01N 33/24
See application file for complete search history.

(56) References Cited

U.S. PATENT DOCUMENTS

2014/0163883 A1* 6/2014 Granjeon .............. G01V 20/00 702/2
2017/0167230 A1* 6/2017 Ducros .................. E21B 41/00
(Continued)

OTHER PUBLICATIONS

Antia et al. (Dec. 2001) "Basin-wide particulate carbon flux in the Atlantic Ocean: Regional export patterns and potential for atmospheric C02 sequestration. Global Biogeochemical Cycles", Global Biogeochemical Cycles, 15(4):845-862.
(Continued)

*Primary Examiner* — Chuen-Meei Gan
(74) *Attorney, Agent, or Firm* — Morrison & Foerster LLP

(57) ABSTRACT

The invention relates to the method of exploration at well level (one-dimensional) of the content and quality of organic matter in source rocks in marine environments. The method for determining the content and maturation of organic carbon by (multi)one-dimensional simulation makes it possible to estimate the production, preservation and degradation of this carbon in a given well (or multiple wells) located in a
(Continued)

sedimentary basin, in order to characterize the organic facies present in the marine environment.

12 Claims, 9 Drawing Sheets

(56) References Cited

U.S. PATENT DOCUMENTS

2018/0313807 A1* 11/2018 Michael .................. E21B 43/30
2018/0355702 A1* 12/2018 Chauveau ............. G01V 11/00

OTHER PUBLICATIONS

Bergamaschi et al. (Mar. 1997) "The Effect of Grain Size and Surface Area on Organic Matter, Lignin and Carbohydrate Concentration, and Molecular Compositions in Peru Margin Sediments", Geochimica et Cosmochimica Acta, 61(6):1247-1260.
Bessereau et al. (Jan. 1, 1995) "Source Rock Occurrence in a Sequence Stratigraphic Framework: The Example of the Lias of the Paris Basin", Paleogeography, Paleoclimate, and Source Rocks, 40:273-301.
Bjerrum et al. (May 10, 2006) "Modeling Organic Carbon Burial During Sea Level Rise with Reference to the Cretaceous", Geochemistry, Geophysics, Geosystems, 7(5):24 Pages.
Carpentier et al. (May 1, 1991) "Wireline Logging And Source Rocks—Estimation of Organic Carbon Content by The Carbolbg@ Method", The Log Analyst, 32(3).
Dahl et al. (Nov. 2004) "A New Approach to Interpreting Rock-Eval S2 and COT Data for Kerogen Quality Assessment", Organic Geochemistry, 35(11-12):1461-1477.
Jarvie, Daniel M. (Jan. 2012) "Shale Resource Systems for Oil and Gas: Part 1—Shale-Gas Resource Systems", American Association of Petroleum Geologists, 69-87.
Justwan et al. (Jan. 2005) "Quantitative Hydrocarbon Potential Mapping and Organofacies Study in the Greater Balder Area, Norwegian North Sea", Geological Society London Petroleum Geology Conference, 1317-1329.
Mann et al. (Nov. 28, 2008) "Modelling Source-Rock Distribution and Quality Variations: The Organic Facies Modelling Approach", Analogue and Numerical Modelling of Sedimentary Systems: From Understanding to Prediction, 40:239-274.
Müller et al. (Dec. 1979) "Productivity, Sedimentation Rate, and Sedimentary Organic Matter in the Oceans—I. Organic Carbon Preservation", Deep Sea Research Part A. Oceanographic Research Papers, 26(12):1347-1362.
Passey et al. (Dec. 1990) "A Practical Model for Organic Richness from Resistivity Logs", American Association of Petroleum Geologists Bulletin, 74(12):1777-1794.
Schwarzkopf, Thomas A. (1993) "Model for Prediction of Organic Carbon Content in Possible Source Rocks", Marine and Petroleum Geology, 10(5):478-492.
Stein et al. (Jul. 30, 1986) "Accumulation of Organic-Carbon-Rich Sediments in the Late Jurassic and Cretaceous Atlantic Ocean—A Synthesis", Chemical Geology, 56(1-2):1-32.
Tissot et al. (1984) "Diagenesis, Catagenesis and Metagenesis of Organic Matter", Petroleum Formation and Occurrence, 69-73.
Tyson R. V. (Jan. 1, 2005) "The "Productivity Versus Preservation" Controversy: Cause, Flaws, and Resolution", The Deposition of Organic-Carbon-Rich Sediments: Models, Mechanisms, and Consequences, SEPM Society for Sedimentary Geology, 82.
Jones, R. W. Organic Facies, in: Brooks, J., Welte, D. (Eds.), Advances in Petroleum Geochemistry. Academic Press, London, 1987, p. 78-80.

* cited by examiner

A
B
1
2
3
4
5
6
C
7
8
9
10
11
D
E
12
13
14
F

G
H
15
16
17
18
19
20
I
J
K
21
22
23
24
L
25
26
27
M
N
28
29
30
31
32
33
34
O

COTr [rock]
COT simulated
Depth [m]
2000
2500
3000
3500
4000
4500
5000
5500
0
1
2
3
4
5
6
7
COT [%]
Anoxic events
Late Cretaceous A
B
C
Depth [m]
2000
2500
3000
3500
4000
4500
5000
5500
220 240 260 280 300 320 340
IH [mg HC/g COT]
120 130 140 150 160 170 180
IO [mg $CO_2$/g COT]
-23.0 -22.0 -21.0 -20.0
$\delta^{13}C$ [‰]

Active carbon [%]
Inactive carbon [%]
Initial active hydrogen index [mg HC/g COT]
Depth [m]
Transformation rate [v/v]
Initial total organic carbon [%]
Initial S2 [mgHc/g rock]
Vitrinite reflectance [%]

COTr [rock]
COT simulated
COT0 [initial]
Depth [m]
2000
2500
3000
3500
4000
4500
5000
5500
0
1
2
3
4
5
6
7
COT [%]
Anoxic events
Late Cretaceous

METHOD FOR DETERMINING THE CONTENT, QUALITY AND MATURATION OF ORGANIC MATTER IN MARINE ENVIRONMENT FOR EXPLORATION OF OIL WELLS

CROSS-REFERENCE TO RELATED APPLICATION

This application claims priority to Brazilian Application No. BR 10 2021 025711 3, filed on Dec. 18, 2021, and entitled "METHOD FOR DETERMINING THE CONTENT, QUALITY AND MATURATION OF ORGANIC MATTER IN MARINE ENVIRONMENT FOR EXPLORATION OF OIL WELLS," the disclosure of which is incorporated herein by reference in its entirety.

FIELD OF THE INVENTION

The present invention pertains to the field of the oil and gas industry, specifically with regard to the study of marine source rocks from the post-salt of the Brazilian shore. Currently, the main objectives of oil exploration are:

i. minimize exploratory risks;

ii. provide better estimates of the potential of source rocks to improve modeling of oil systems;

iii. expand oil exploration to deep and ultra-deep marine environments.

In this context, it becomes increasingly necessary to develop new processes that seek to help the oil sector to achieve these objectives.

DESCRIPTION OF THE STATE OF THE ART

The technical problem that motivated the invention was the need of obtaining better estimates of the content and quality of organic matter in order to improve the characterization of organic facies in a sedimentary basin, reducing exploratory risks and increasing understanding about the processes linked to the production, preservation and degradation of organic matter in the marine environment.

The methods of simulating the content and maturation of organic carbon aim at estimating the production, preservation and degradation of this carbon in a given well (or multiple wells) located in a sedimentary basin, in order to characterize the organic facies present in the marine environment. Previous works were developed with the intention of simulating the total organic carbon content in a one-dimensional scale (well level). Among the main pioneer works we can mention the studies of: PASSEY, Q. R.; CREANEY, S.; KULLA, J. B.; MORETTI, F. J.; STROUD, J. D. A Practical Model for Organic Richness from Porosity and Resistivity Logs. AAPG Bulletin, [S. I.], v. 74, n. 12, p. 1777-1794, 1990; and CARPENTIER, B.; HUC, A. Y.; BESSEREAU, G. Wireline Logging And Source Rocks—Estimation Of Organic Carbon Content By The Carbolbg@ Method. The Log Analyst, [S. I.], v. 32, n. 03, 1991. These approaches were focused on processes that used data from geophysical well logs to estimate total organic carbon. In the method developed by Passey et al. (1990), also called Δ log R, resistivity and porosity profiles of wells are used to estimate the total organic carbon content. The technique is based on the logic that the curves of the two used geophysical profiles deviate with the presence of organic matter in a given layer, which occurs due to a change in porosity. Another classic method is the one developed by Carpentier et al. (1991), also known as CARBOLOG®, which, like Passey et al. (1990), employs conventional geophysical profiles. However, in the case of the CARBOLOG® method, sonic and resistivity profiles are used to also generate estimates of total organic carbon content. This method is based on the principle that the higher the values of the sonic profile and the lower the values of the resistivity profile, the greater the proportion of clay or water in the layer, while the opposite indicates a greater content of organic matter.

Later, other approaches emerged with the aim of simulating the organic carbon content on a one-dimensional scale. The method of SCHWARZKOPF, Thomas A. Model for prediction of organic carbon content in possible source rocks. Marine and Petroleum Geology, [S. I.], v. 10, n. 5, p. 478-492, 1993, does not use geophysical logging data as input data. Instead, it uses environmental variables such as primary productivity in the ocean, water column depth and sedimentation rate. Based on these data, a simulation is run using the Monte Carlo method, thus generating a probabilistic distribution of the total organic carbon content. In the study by BESSEREAU, G.; GUILLOCHEAU, F.; HUC, A. Y. Source rock occurrence in a sequence stratigraphic framework: the example of the Lias of the Paris Basin. In: HUC, A. Y. (org.). Paleogeography, paleoclimate, and source rocks. The American Association of Petroleum Geologists, Houston: AAPG; Studies in Geology, 40, 1995. p. 273-301, the method is based on the correlation between organic matter and the stratigraphy approach of sequences, where intervals rich in organic matter are associated with surfaces of maximum flooding and with the end of retrogradation and the beginning of progradation in the system. In addition, studies such as those by BJERRUM, C. J.; BENDTSEN, J.; LEGARTH, J. J. F. Modeling organic carbon burial during sea level rise with reference to the Cretaceous. Geochemistry, Geophysics, Geosystems, [S. I.], v. 7, n. 5, 2006, applied biogeochemical models to estimate the carbon content in marine sediments, in an approach that is an extension of the classic box model for the ocean. In this case, differential equations are used to solve the biogeochemical processes in each model box. One of the most recent methodologies to simulate the total organic carbon content in source rocks is the one used by the model MANN, Ute; ZWEIGEL, Janine. Modeling Source-Rock Distribution and Quality Variations: The Organic Facies Modeling Approach. In: Analogue and Numerical Modeling of Sedimentary Systems: From Understanding to Prediction. [S. I.]: John Wiley & Sons, Ltd, 2008. p. 239-274, which allows estimating the distribution and quality of organic matter. This model also uses environmental variables as input data, and through a sequence of steps using a unique and determined set of equations calculates the total organic carbon content in one-dimensional scale, or in 3D scale of sedimentary basin if it is coupled to a model stratigraphic.

Thus, only the process described in this patent application simulates the content and quality of organic matter on a (multi)one-dimensional scale through a sequence of steps that allows the choice and coupling of different equations. FIG. 1 represents the process in steps of simulating the content and quality of organic matter, while FIG. 2 presents the steps of the process referring to the maturation level of the organic matter. Accordingly, none of the previous methods considers both the content and the quality of the organic matter in a one-dimensional process that allows the coupling of different equations along the sequence of innovative steps. In addition, the method described here has its own equations and methodologies embedded in its simulation process. The input data for the total organic carbon and organic matter quality simulation process are depth, sedimentation rate, primary productivity, dry apparent density, bathymetry and sand fraction. In the case of the simulation process of the organic carbon maturation stage, input data from geochemical analyses and Rock-Eval pyrolysis are used. The process described here can also be coupled to a stratigraphic model for simulation at other scales (3D, for example).

Objective of the Invention

The invention described here aims at providing a method based on (multi)one-dimensional simulations of the content and quality of organic matter. The method is based on a sequence of logical steps that allow the choice and coupling of different equations within the simulation process. The invention allows the identification of sedimentary layers rich in organic carbon in marine environments, also elucidating the organic fractions that make up the simulated total organic carbon, which helps oil exploration, especially in deep and ultra-deep marine environments.

BRIEF DESCRIPTION OF THE INVENTION

The invention refers to the method of exploration at well level (one-dimensional) of the content and quality of organic matter in source rocks in marine environments. The method for determining the content and maturation of organic carbon by (multi)one-dimensional simulation makes it possible to estimate the production, preservation and degradation of this carbon in a given well (or multiple wells) located in a sedimentary basin, in order to characterize the organic facies present in the marine environment. The method developed by the present invention has two modules: Total Organic Carbon Module and Maturation Module. The result obtained in these two modules allows decision-making regarding the exploration of a well.

BRIEF DESCRIPTION OF THE DRAWINGS

The present invention will be described in more detail below, with reference to the attached figures which, in a schematic way and not limiting the inventive scope, represent examples of its embodiment. In the drawings, there are.

DETAILED DESCRIPTION OF THE INVENTION

There follows below a detailed description of a preferred embodiment of the present invention, by way of example and in no way limiting. Nevertheless, it will be clear to a technician skilled on the subject, from reading this description, possible additional embodiments of the present invention still comprised by the essential and optional features below.

Figure 1:
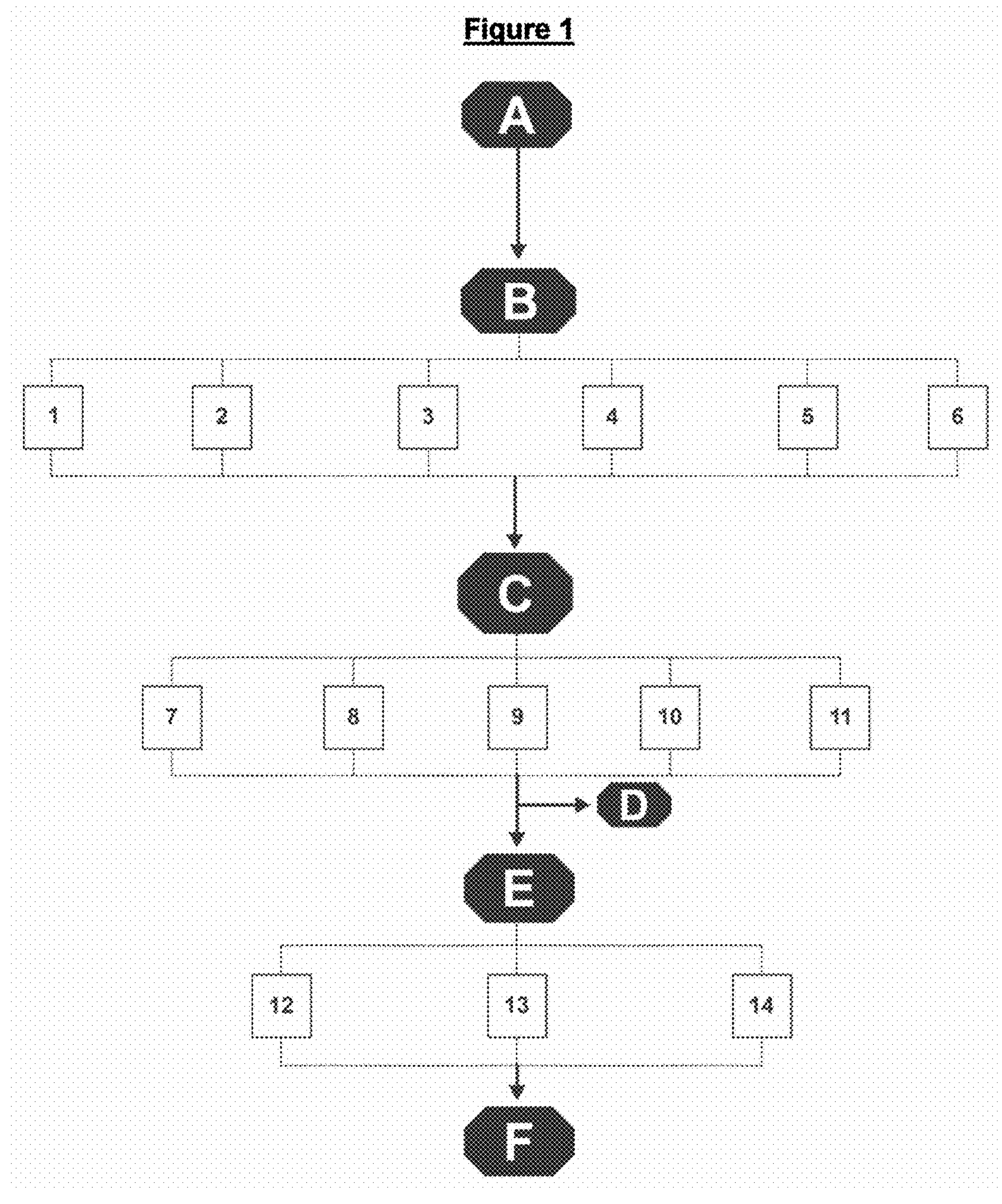
FIG. 1 illustrates the steps in the first module (Total Organic Carbon Module), wherein there are represented: Total Organic Carbon (COT) content simulation process on a (multi)one-dimensional scale (A), input environmental variables (B), the depth [m]/ages [MA] (1), sedimentation rate [cm/ka] (2), the primary productivity [gC/m$^2$ year] (3), bathymetry/paleopathometry [m] (4), dry apparent density [g/cm$^3$] (5), sand fraction [%] (6), definition of equations for estimating Total Organic Carbon (C), marine organic carbon [$CO_{ma}$] (7), terrestrial organic carbon [$CO_{TE}$] (8), carbon flux (9), burial efficiency [E] (10), Anoxia/preservation factor [PF] (11), export of results (D), mixture model for organic matter quality (E), hydrogen index reference values (12), oxygen index reference values (13), $^{13}$C reference values (14), export of results (F).
Figure 2:
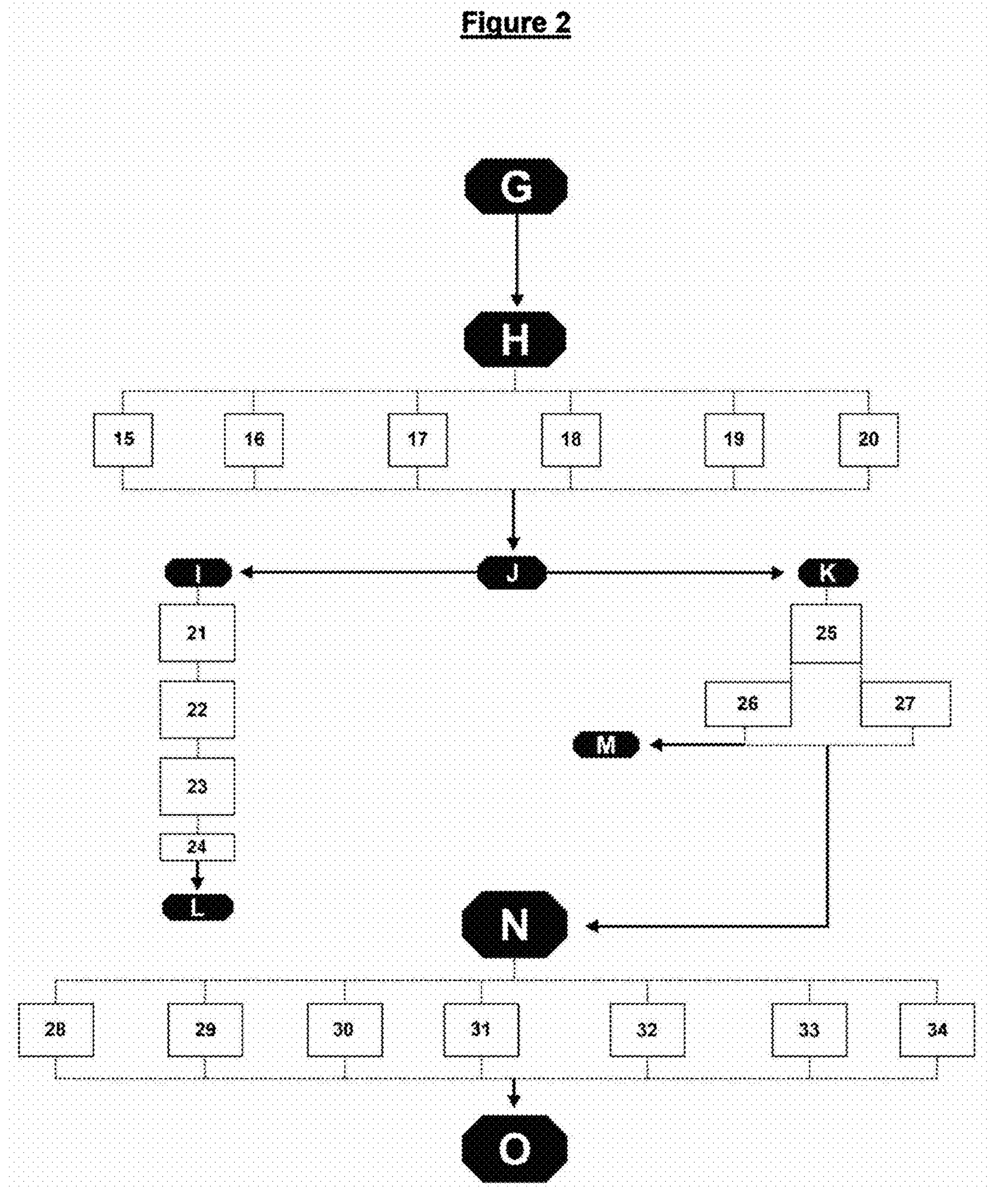
FIG. 2 illustrates the steps of the second module (Maturation Module), wherein there are represented: Process of simulating the maturation of organic matter on a (multi)one-dimensional scale (G), input laboratory variables (H), depth [m]/ages [Ma] (15), S1 [mg Hc/g rock] (16), S2 [mg Hc/g rock] (17); vitrinite reflectance [R %] (18), total organic carbon in the rock [%] (19), maximum temperature [%] (20), evaluations (I), pre-processing (J), grouping (K), poor, moderate, good, excellent amount of organic matter S2 vs COT (21), quality of organic matter IH vs IO kerogen type I, II, III, IV (22), thermal maturation maximum temperature vs Ro immature, mature, overmature (23), relative potential of hydrocarbons (24), export of results (L), total organic carbon vs S2 (25), total active organic carbon (26), total inert organic carbon (27), export of results (M), definition of maturation parameter equations (N), active organic carbon [%] (28), inert organic carbon [%] (29), transformation rate (30), initial total organic carbon [%] (31), initial hydrogen index [mg Hc/g COT] (32), initial S2 [mgHc/g rock] (33), vitrinite reflectance [%] (34).

The one-dimensional organic carbon simulation process is a sequence of logical calculation steps using multiple equations that aims at estimating the amount and quality of organic carbon at the well level (FIG. 1). The method described here mainly considers the production, preservation, degradation and maturation of organic carbon. To this end, the process is divided into two modules, the Total Organic Carbon Module (FIG. 1) and the Maturation Module (FIG. 2). In each module, a series of logical steps established by this invention make it possible to elucidate the environmental processes linked to carbon deposition in marine environments. The simulation requires input data specific to the location of a given exploratory well, and uses regression-based and/or process-based equations to estimate the amount and quality of total organic carbon. These estimates can be carried out for time scales of the order of hundreds of millions of years, which is important for the area of oil exploration.

In the Total Organic Carbon Module, the objective is to carry out the production and preservation of organic carbon in different organic fractions, as well as to generate an initial estimate of the quality of this simulated organic carbon. The organic carbon deposited in marine environments can come from the terrestrial environment (allochthonous) or from the marine environment itself (autochthonous). Autochthonous organic carbon comes from primary productivity and carbon flux, that is, it is the result of planktonic biomass (phytoplankton and zooplankton), as well as bacteria, and also organic detritus. Allochthonous organic carbon comes from vascular plants and plant remains, transported by river or wind, and may be derived from recent primary production or may have been reworked and diagenetically altered. The preservation of the terrestrial and marine fractions of organic carbon will depend on the conditions present in the depositional environment. In this way, the present invention manages to quantify these organic fractions, taking into account information about the depositional environment, and finally estimates the total organic carbon content, as well as the quality of this carbon based on the proportion between the fractions (terrestrial and marine) that make up the total.

In the Maturation Module, the objective is to estimate the processes linked to advanced diagenesis and catagenesis, which ultimately relate to the quality and maturation process of organic carbon (FIG. 2). Changes in the chemical composition of sediments after deposition are known as diagenesis. In the catagenesis process, hydrocarbons and compounds such as resins and asphaltenes are generated by thermal cracking. Thermal maturation can be defined as chemical changes in the sedimentary organic matter due to the increase in temperature due to the advance in burial. In this way, the present invention is able to estimate important parameters related to the maturation process of organic carbon, taking into account data from geochemical analyses and Rock-Eval pyrolysis.

This method comprises the following steps in the first module (Total Organic Carbon Module):

1. Supply of input data for environmental variables (depth, sedimentation rate, primary productivity, dry apparent density, bathymetry and sand fraction) for the studied well;
2. Determination of equations for calculating marine organic carbon, which may include calculations of carbon flux and burial efficiency depending on the chosen method, and calculation of terrestrial organic carbon, where two fractions of terrestrial organic carbon are calculated;
3. Quantification of the total organic carbon content of the well;
4. Estimation of organic matter quality through a mixture model, using reference values for the calculated organic fractions.

The same way, there are the following steps in the second module (Maturation Module):

1. Supply of input data from geochemical and Rock-Eval pyrolysis analyses, which are: S1, S2, S3, temperature at which the maximum rate of hydrocarbon generation occurs in a kerogen sample, vitrinite reflectance, total organic carbon measured in rock;
2. Evaluation of input data in relation to generation potential, kerogen type, thermal maturation and relative hydrocarbon potential;
3. Grouping data into subsets to estimate active organic carbon and inert organic carbon for each data subset;
4. Determination of the equations for the calculation of initial hydrogen index, initial active hydrogen index, transformation rate, initial total organic carbon, initial S2 and calculated vitrinite reflectance;
5. Evaluation of the quality of the organic matter through the calculated parameters.

In this way, with the simulation results from the modules that make up the well-level exploration method (one-dimensional) of the content and quality of organic matter in source rocks in marine environments, it is possible to determine the total organic carbon content and its maturation process. From the results obtained, it is then possible to establish the organic facies present in each layer. The result obtained in these two modules allows decision-making regarding the exploration of a well.

The production of marine organic carbon can be estimated using multivariate equations of the type $$COma = \frac{a*PP*SRb}{DBD},$$

where COma is the marine organic carbon, PP is the primary productivity, SR is the sedimentation rate, DBD is the dry apparent density, and finally a and b are constant values specific to the equation. It can also be from equations that include regression of factors and processes, such as $$COma = \frac{a*CF}{DBD*sRb},$$

where COma is marine organic carbon, CF is carbon flux, SR is the sedimentation rate, DBD is the dry apparent density, and finally a and b are constant values specific to the equation. And finally, marine organic carbon can also be estimated from equations that include only processes, such as $$COma = \frac{(BE*CF)}{(BE*CF+DBD*SR*10)*100},$$

where COma is marine organic carbon, BE is the burial efficiency, CF is the carbon flux, SR is the sedimentation rate, and DBD is the dry apparent density. In the case of equations that use the processes of carbon flux and/or burial efficiency, a range of equations available in the simulation process can be chosen. To calculate the carbon flux, an example structure is CF=a*WDb*PPc, where CF is the carbon flux, WD is the depth of the water column, PP is the primary productivity, and a and b are constant values specific to the equation. In the case of burial efficiency, an example of a calculation structure is $$\log 10\left(\frac{BE}{100}\right) = \frac{a*\log 10SR}{\log 10(SR+b)} + c,$$

where BE is the burial efficiency, SR is the sedimentation rate and a, b and c are constant values specific to the equation. The marine organic carbon production can also be estimated for anoxic conditions, which follows the following equation COma=(PP*PF)/(DBD*SR), where COma is the marine organic carbon, PP is the primary productivity, PF is the carbon preservation factor under anoxic conditions, SR is the sedimentation rate, and DBD is the dry apparent density of the sediment.

The next step of the method is the simulation of terrestrial organic carbon production. In this step, two terrestrial organic fractions are calculated, the terrestrial organic carbon corresponding to kerogen (qCO), and the residual terrestrial organic carbon (rCO). These fractions are calculated from the sand fraction input data, and can have two types of production regimes, the high regime and the low regime, which represent the level of terrestrial organic carbon production. In both regimes, the structure for calculating fractions is rCO=a*SF+b, where rCO is the residual terrestrial organic carbon, SF is the sand fraction in percent, and a and b are constant values specific to the equation. In the case of the other terrestrial organic fraction, there is a conditional logic, if FA<75%, qCO=a*FA, if FA>=75%, qCO=a*FA+b, where qCO is terrestrial organic carbon, FA is the sand fraction in percent, and a and b are constant values specific to the equation.

At the end of these steps, the marine and terrestrial organic fractions will have been quantified. From the quantifications of each organic fraction, it becomes possible to apply a three-source mixture model to estimate the values of hydrogen index, oxygen index and carbon isotopic signature. To this end, reference values are defined for each fraction, and these values are multiplied by the amounts of each fraction, so that a final average value is estimated for each of the parameters mentioned above in the well layers. For example, IO=IOCOma*COma+IOqCO*qCO+IOrCO*rCO, where IO is the calculated oxygen index for a given layer, IOCOma is the reference oxygen index value for marine organic carbon, COma is the amount of marine organic carbon that was previously calculated, IOqCO is the oxygen index reference value for terrestrial organic carbon, qCO is the amount of terrestrial organic carbon that was previously calculated, IOrCO is the oxygen index reference value for residual terrestrial organic carbon, and rCO is the amount of residual terrestrial organic carbon that was previously calculated.

In the Maturation Module, the processes of advanced diagenesis and catagenesis are contemplated in the simulation by calculating the total inert organic carbon, total active organic carbon, active hydrogen index, transformation rate, initial total organic carbon, initial S2, initial hydrogen index, and calculated vitrinite reflectance. The objective of this module is to estimate these parameters from a sequence of steps in order to evaluate the amount, quality and maturation of organic carbon. The mentioned parameters are calculated from the depth data, S1, S2, hydrogen index, vitrinite reflectance, total organic carbon measured in the rock, and maximum temperature of the samples from a given well. Thus, a sequence of logical steps is established in the simulation process to estimate the parameters of interest.

An initial phase of evaluating the input data and data grouping in a clustering process is carried out. Groupings are then analyzed from total organic carbon data measured in the rock and S2. For each grouping, a linear regression is performed, and from the intercept value of the line, the total active organic carbon and the total inert organic carbon are calculated. If the intercept is equal to zero, the total active organic carbon is equal to the total organic carbon measured in the rock. In case the intercept value of the line is different from zero, the equation Cativo=COTr−Cinerte is applied, where Cativo is the total active organic carbon, COTr is the measured total organic carbon in the rock, and Cinerte is the total inert organic carbon. From the calculation of Cativo, the active hydrogen index is calculated using the equation $$IH0ativo = 100 * \frac{S2}{Cativo},$$

where IH0ativo is the active hydrogen index and Cativo is carbon active total organic. Subsequently, with the calculation of the IH0ativo performed, it is possible to estimate the transformation rate following the equation $$TR = \frac{IH0ativo - 1}{IHativo},$$

where TR is the transformation rate, IH0ativo is the initial active hydrogen index, and IH is the hydrogen index. If the value of TR is greater than zero, the method can proceed to calculate the initial total organic carbon, using the equation $$COT0 = COTr + \left[S2 * \frac{Tr}{1 - Tr}\right] * a,$$

where COT0 is the initial total organic carbon, COTr is the total organic carbon measured in the rock, TR is the transformation rate, and a is a defined factor. It is also possible at this stage of the process to simulate the initial S2 value from $$S20 = \frac{S2}{1 - Tr},$$

where S20 is the initial S2, and TR is the transformation rate. After estimating the S20, it is possible to proceed to the next step of the process and calculate the initial hydrogen index using the equation $$IH0 = \frac{S20}{COT0},$$

where IH0 is the initial hydrogen index, S20 is the initial S2, and COT0 is the initial total organic carbon. Additionally, at the end of the process it is possible to obtain the calculated vitrinite reflectance, using R0=(a*Tmax)−b, where R0 is the calculated vitrinite reflectance, Tmax is the maximum temperature, and a and b are constant values specific to the equation. From the results obtained in both modules, it is possible to classify the organic facies by layers at the well level, using the calculated parameters and reference tables for classification of organic facies.

FIG. 1 shows the flowchart with the steps related to the simulation of total organic carbon by the invention (first module—Total Organic Carbon Module). FIG. 1 shows the steps of the method themselves (black boxes) and the input environmental variables or predictive equations (white boxes).

FIG. 2 shows a flowchart with the steps related to the simulation of maturation of organic matter by the invention (second module—Maturation Module). FIG. 2 shows the method steps themselves (black boxes) and the input environmental variables or predictive equations (white boxes).

Figure 3:
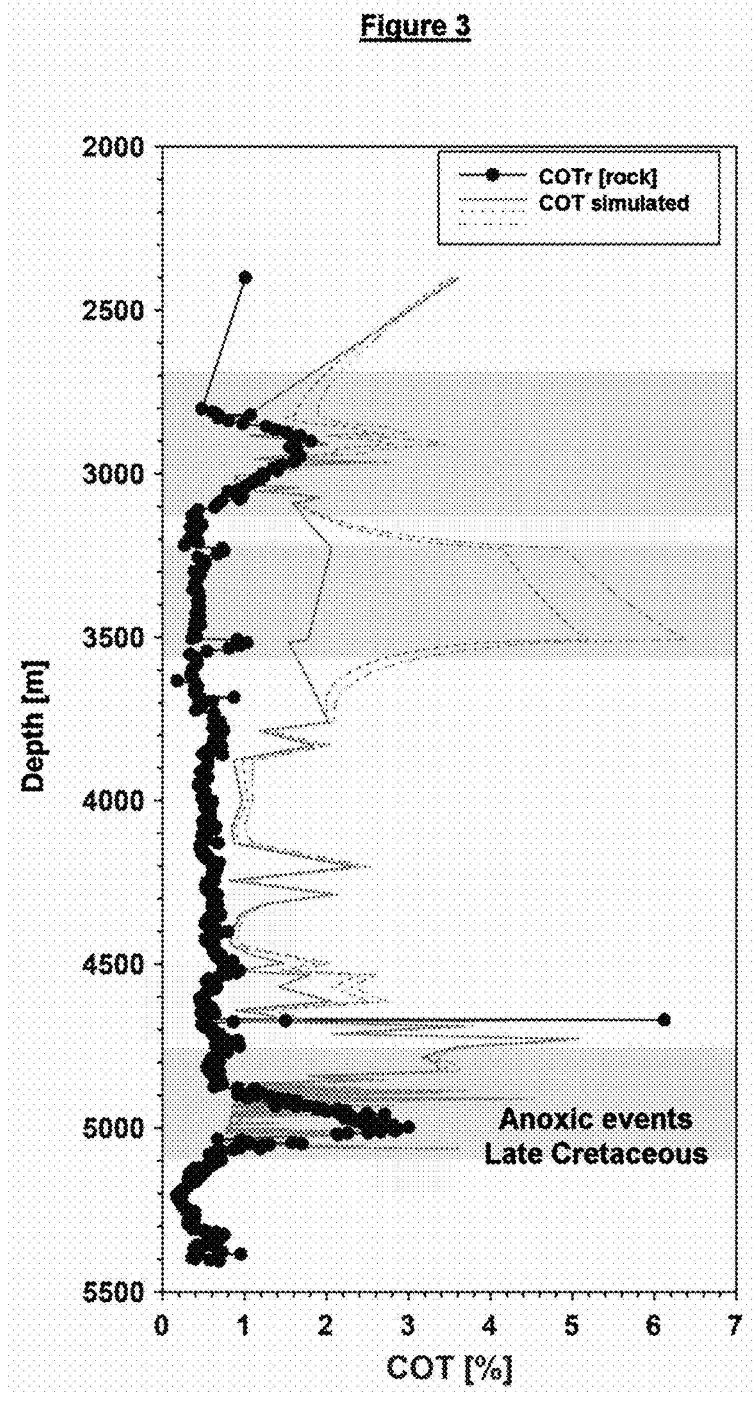
FIG. 3 compares the results obtained in a simulation of the total organic carbon by the invention with the total organic carbon measured in the rocks of an exploratory well in the Espirito Santo basin.

FIG. 3 compares the results obtained in a simulation of the total organic carbon by the invention (solid, dashed, and dotted dashed lines) with the total organic carbon measured in the rocks of an exploratory well in the Espirito Santo basin (black line with dots). The total organic carbon was simulated using the three marine organic carbon equations available in the invention. As explained in the section, it is still necessary to carry out the maturation stage so that the comparison is more reliable, but it is already possible to notice some intervals in which the simulation process approaches the actual values found in the well relatively well.

Figure 4:
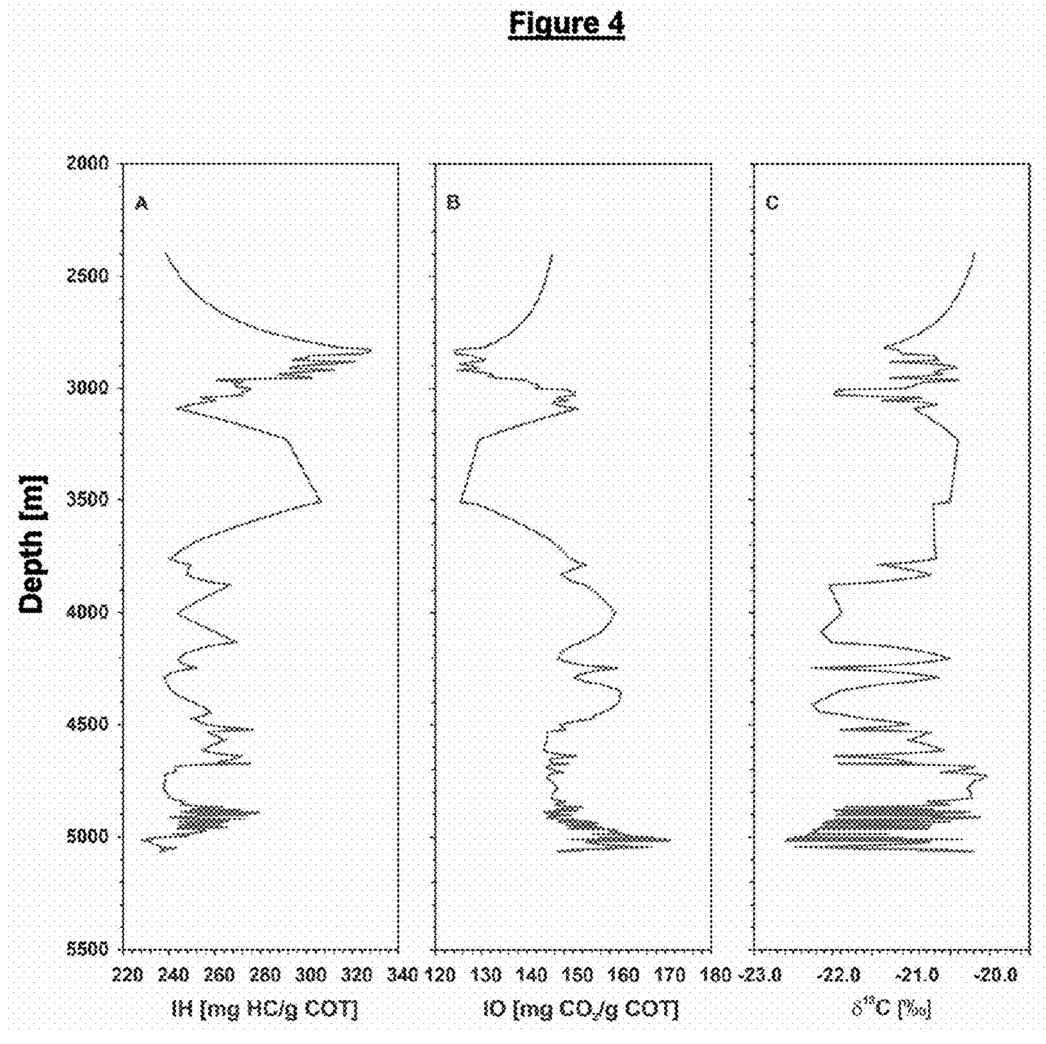
FIG. 4 represents the result referring to the quality of the organic matter obtained at the end of the simulation process of the total organic carbon of the exploratory well.

FIG. 4 represents the result regarding the quality of the organic matter obtained at the end of the simulation process of the total organic carbon of the exploratory well in question. Panels 4A, 4B and 4C present the distribution of Hydrogen index, Oxygen index and isotopic composition of the organic carbon, respectively.

Figure 5:
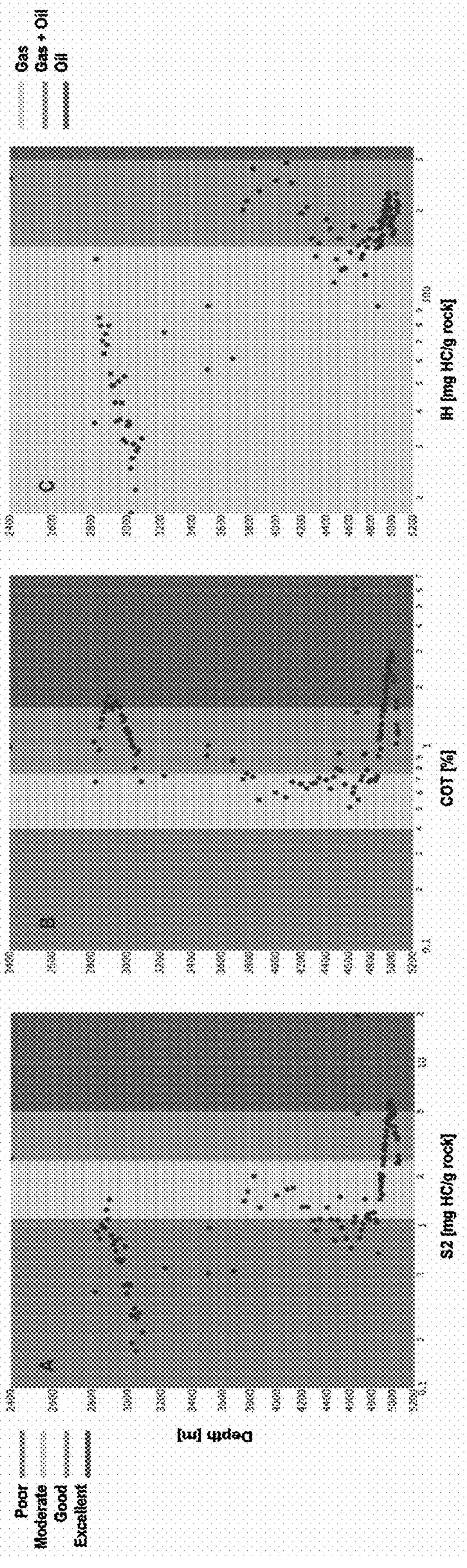
FIG. 5 illustrates the result of the pre-evaluation regarding the distribution of the generating potential of the rocks in the exploratory well under analysis.
Figure 5:

FIG. 5 highlights the result of the pre-evaluation regarding the distribution of the generating potential of the rocks in the exploratory well under analysis. Based on S2 and the total organic carbon, the method hierarchizes the potential between "Poor" and "Excellent" (panels 5A and 5B). Based on the Hydrogen index, the invention ranks the potential between "Gas", "Gas+Oil" and "Oil" (panel 5C).

Figure 6:
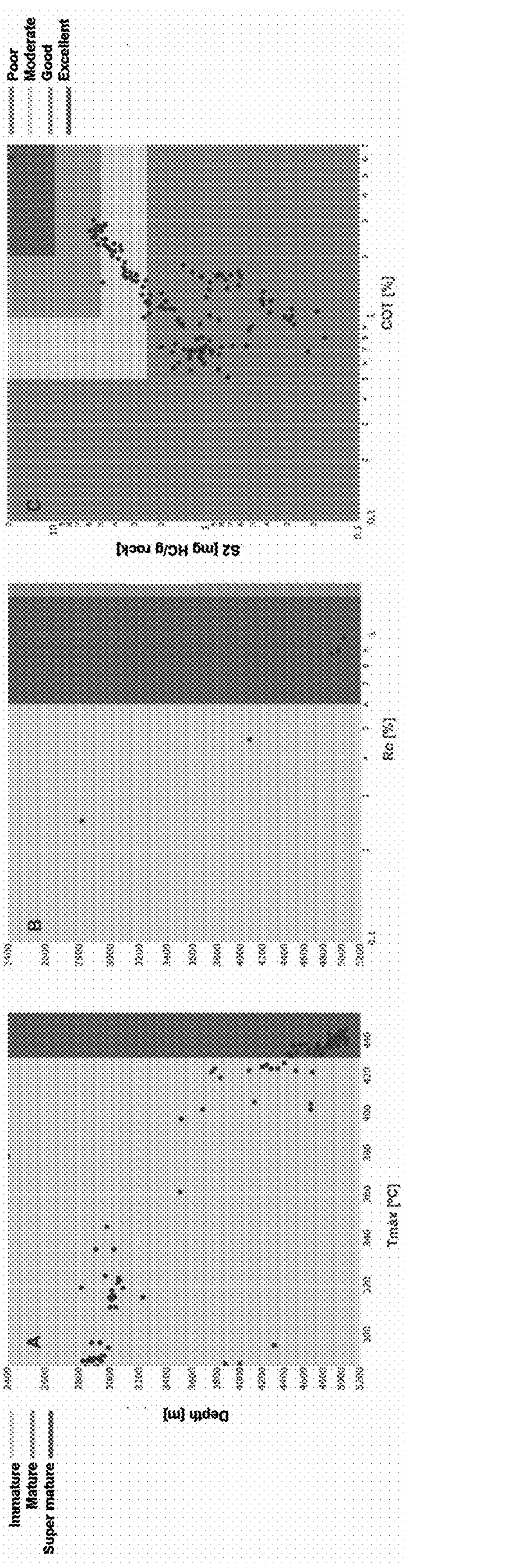
FIG. 6 illustrates the result of the pre-evaluation regarding the distribution of the generating potential of the rocks in the exploratory well under analysis.

FIG. 6 shows the result of the pre-evaluation regarding the distribution of the generating potential of the rocks in the exploratory well under analysis. Based on the maximum temperature and reflectance of the vitrinite, the invention hierarchizes the potential between "Immature" and "Super mature" (panels 6A and 6B). Based on the correlation between total organic carbon in rocks and S2, the invention ranks the potential between "Poor" and "Excellent" (panel 6C).

Figure 7:
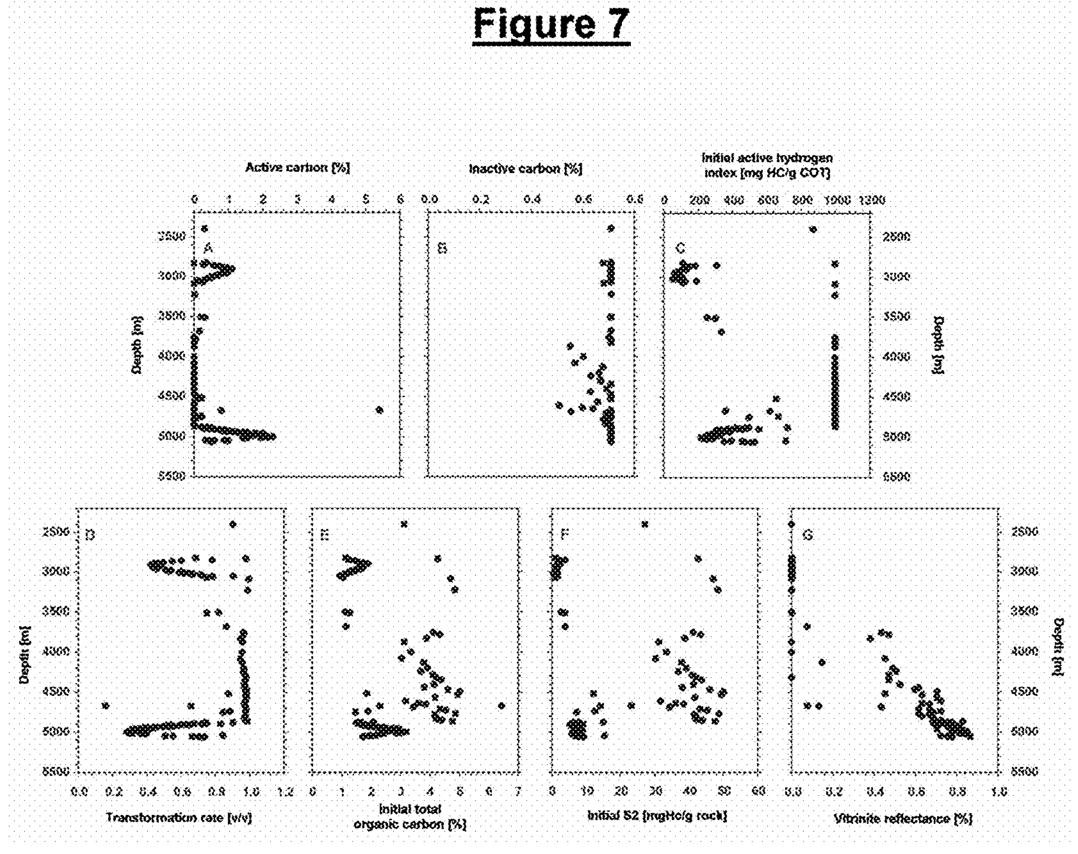
FIG. 7 illustrates the final result of the process of simulating the maturation of the organic matter of the rocks in the exploratory well under analysis.

FIG. 7 shows the final result of the simulation of the maturation of the organic matter of the rocks in the exploratory well under analysis. Panels 7A-G represent each of the parameters returned by the invention: active carbon, inert carbon, transformation rate, initial total organic carbon, initial active Hydrogen index, initial S2, calculated vitrinite reflectance.

Figure 8:
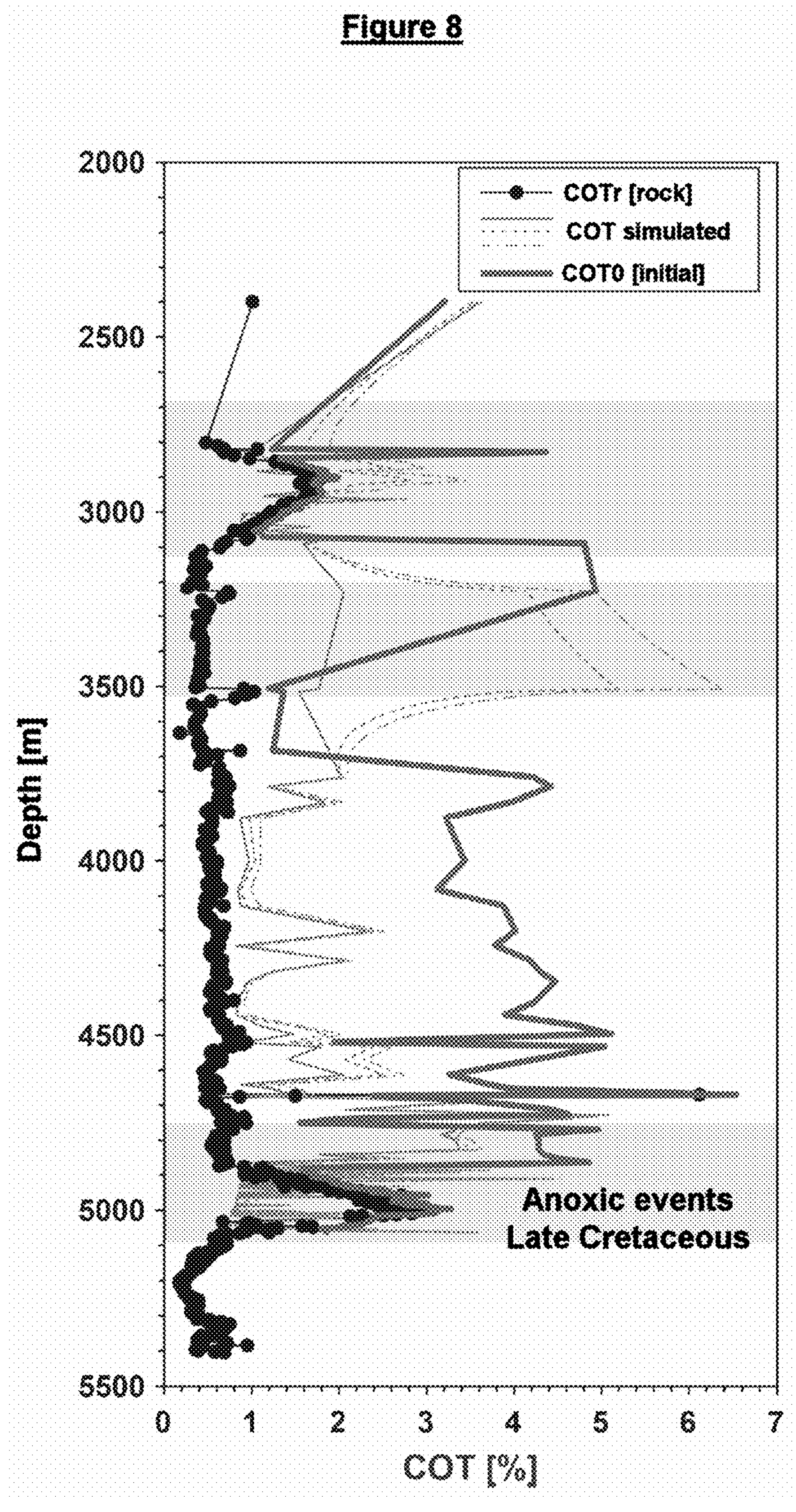
FIG. 8 illustrates a comparison of the results obtained in a simulation of the total organic carbon by the invention, the total organic carbon measured in the rocks and the initial total organic carbon measured after the simulation of the maturation of the organic matter.

FIG. 8 compares the results obtained in a simulation of the total organic carbon by the invention (thin solid, dashed and dotted dashed lines), the total organic carbon measured in the rocks (black line with dots) and the initial total organic carbon (thick solid line) measured after simulation of organic matter maturation. Note that, unlike what is shown in FIG. 3, when considering the degradation processes of organic matter over geological time, the simulation process by the invention becomes more adherent to the value of organic carbon measured in the rocks.

Figure 9:
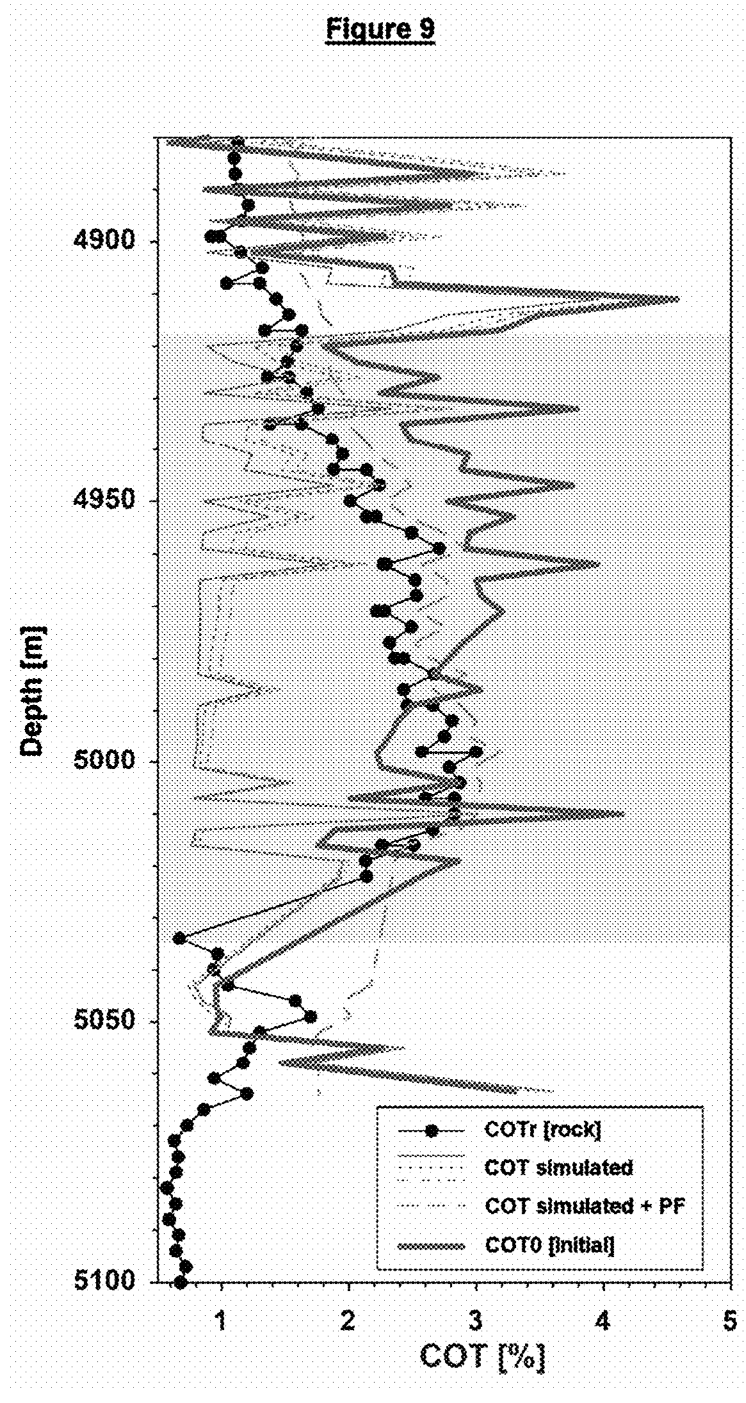
FIG. 9 illustrates a comparison of the results obtained in a simulation of total organic carbon by the invention with the inclusion of the "preservation factor" process.

FIG. 9 shows a comparison with the results obtained in a simulation of the total organic carbon by the method developed in the present invention (thin solid, dashed and dotted dashed lines), the total organic carbon measured in the rocks (black line with dots), the initial total organic carbon (thick solid line) measured after simulating the maturation of the organic matter and the total organic carbon simulated by the invention using a preservation factor (long dashed line) to indicate the presence of an anoxic event between the stratigraphic depths of 5100-4890 m of the rocks from the exploratory well under analysis. Note that, when assuming an event of reduced oxygenation in the depositional environment, the simulation result becomes more adherent to the measured organic carbon value in the rocks (area highlighted in gray). At the end of this event, conventional simulations perform better.

Next, there will be described in more detail the processes and steps contained in the Total Organic Carbon Module and the Maturation Module.

This section defines the acronyms of the main terms used in this document. Given the relatively large number of terms, to facilitate understanding, the acronyms defined in this section are eventually repeated throughout the document. Therefore, the following annotations are employed:

1. BE—Burial Efficiency. Indicates the amount of Organic Carbon that is effectively buried in the water-sediment interface (Burial Efficiency).
2. Cativo—Active Carbon. Portion of Total Organic Carbon (COT) that still can be transformed by Maturation processes to generate oil and/or gas.
3. Cinerte—Inert Carbon. Portion of the Total Organic Carbon (COT) that is degraded or that has already been transformed by the Maturation processes and, therefore, does not have the potential to generate oil and gas.
4. CF—Carbon Flux. Indicates the transport flux of organic carbon generated in the water column to the water-sediment interface where it is deposited (Carbon Flux).
5. Cluster—Grouping data from the Maturation Simulation Module (clustering).
6. COma—Marine Organic Carbon. Autochthonous organic carbon produced on the ocean surface (water column) by the primary productivity of organisms and overlying marine trophic chains.
7. COte—Terrestrial Organic Carbon. Allochthonous organic carbon, of continental origin, which is transported to the ocean basin by hydrodynamic flows.
8. COT—Total Organic Carbon deposited in the original depositional environment. Represents the sum of Marine Organic Carbon (COma) and the fractions rCO and qCO of Terrestrial Organic Carbon (COte).
9. COT0—Total Organic Carbon after the initial stages of diagenesis.
10. COTr—Total organic carbon measured in the rock.
11. DBD—Dry apparent density. It represents the mass of a solid (rock) divided by its dry volume (Dry Bulk Density).
12. IH—Hydrogen Index. Calculated through the ratio between peak hydrocarbons S2 and COTr in the sample. Corresponds to the amount of "pyrolyzable" organic compounds in the sample.
13. IH0—Initial Hydrogen Index. Hydrogen Index calculated for COT0 (post-diagenetic).
14. Active IH0—Active Hydrogen Index. Hydrogen Index of the active fraction of organic carbon (Cativo).
15. IHCma—Marine Carbon Hydrogen Index. Reference value for the Hydrogen content of marine organic carbon.
16. IHqCO—Terrestrial Carbon Hydrogen Index. Reference value for the Hydrogen content of the qCO fraction of terrestrial organic carbon.
17. IHrCO—Hydrogen index of terrestrial carbon. Reference value for the Hydrogen content of the rCO fraction of terrestrial organic carbon.
18. MO—Organic Matter.
19. OCAR—Organic Carbon Accumulation Rate. Represents the ratio of marine organic carbon accumulated in relation to the total sedimentation rate (Organic Carbon Accumulation Rate).
20. OMZ—Minimum Oxygen Zone. Region of the water column depleted in oxygen due to its high consumption, especially in regions of high primary productivity (Oxygen Minimum Zone).
21. PF—Preservation Factor. Preservation index (0-1) used to simulate the occurrence of anoxia events (Preservation Factor).
22. PP—Primary Productivity. Rate of organic matter production by photosynthetic organisms that inhabit the upper portion of the water column.
23. qCO—Fraction of terrestrial organic carbon corresponding to kerogen.

24. R0—Vitrinite reflectance. Petrographic thermal maturation classification index.
25. Calculated R0—Calculated vitrinite reflectance. Index calculated to estimate the vitrinite reflectance of the sample after primary diagenesis. Calculated from the maximum temperature (Tmax).
26. rCO—Fraction of terrestrial organic carbon corresponding to soil residual carbon.
27. S1—Peak in the Rock Eval gradual heating diagram that represents the presence and expulsion of hydrocarbons in the sample.
28. S2—Peak in the Rock Eval gradual heating diagram that represents the generation of hydrocarbons by the cracking of the kerogen in the sample.
29. S20—S2 peak value calculated for the sample after primary diagenesis.
30. SF—Sand Fraction. Percentage of sand contained in the rock.
31. SR—Sedimentation Rate. Sediment accumulation rate (Sedimentation Rate).
32. Tmax Maximum Temperature. Temperature corresponding to the S2 peak of the Rock Eval pyrolysis diagram.
33. TR—Transformation Rate. Ratio between the oil that was generated by the kerogen, in relation to the total oil generation potential from the initial kerogen in the sample/Ratio between the oil generated by the kerogen and the total amount of oil that the initial kerogen was able to generate (Transformation Rate).
34. WD—Bathymetry/Paleobathymetry. Depth of the water column, where positive values represent submerged regions (Water Depth).

The method developed in this invention allows, through a logical sequence of steps, to simulate one-dimensionally (or multi-one-dimensionally) the amount, through the quantification and sum of the fractions of COma and COte that result in the COT, and quality of the organic carbon, through of several parameters such as IH, IO, 513C, among others.

In order to achieve this objective, the following steps are taken:

1. Definition of well entry data for each module;
2. Determination of the equations for each step of the simulation in each module;
3. Prediction of the amount of total organic carbon (Total Organic Carbon Module);
4. Prediction of the previously quantified total organic carbon quality (Total Organic Carbon Module);
5. Evaluation of organic carbon maturation processes (Maturation Module).

In FIG. 1, there is the representation of the simulation method used in this invention. Next, these steps will be described in detail, pointing out the main concepts and calculations that guide the used simulation method.

Definition of Input Data.

Next, the input data definition will be presented. In the Total Organic Carbon Module, the input parameters are environmental variables that define the environmental condition at the location of the well. Environmental parameters are sedimentation rate (SR), primary productivity (PP), dry apparent density (DBD), bathymetry (WD) and sand fraction (SF). These parameters are linked to the depth or age of the well. The primary productivity defines the autochthonous production of carbon in the location of the well, that is, it provides an input for the calculation of the fraction of marine organic carbon (COma). It must be defined according to the productivity in the exploited area, based on a database and previous studies. The sedimentation rate defines the depositional system and how it can contribute to processes such as accumulation, preservation and dilution of carbon content. In environments where the sedimentation rate is very high, greater than 5 cm per thousand years, a dilution effect of the organic material may occur, and consequently the estimated total organic carbon (COT) values will be lower. However, if the sedimentation rate is too low, carbon accumulation may be impaired, as the component related to terrestrial organic carbon (COte) may be relatively small. In addition, if the environment is oxic, that is, favorable to the degradation of organic matter, the low rate of sedimentation causes less burial and, therefore, less preservation of deposited organic carbon. The dry apparent density provides information about the composition of the sediment, which can be very variable in certain depositional environments, and can also vary according to the total organic carbon content. Bathymetry is also an important parameter to characterize the depositional environment at the exploratory well site, as it provides information on the processes of degradation and transport of organic matter. Higher bathymetry values normally indicate greater distance from the coast, and therefore may suggest a lower terrestrial organic carbon component and a higher marine organic carbon component. In addition, a greater bathymetry also results in a greater column of water, which makes the flux of carbon (CF) smaller, since a greater degradation of marine organic carbon occurs due to the time that it is exposed in the water during its transport to the bottom of the ocean. The fraction of sand in a well helps to estimate the degree of the terrestrial component of carbon, since regions closer to the continent have higher contents of sand in relation to silt and clay. Accordingly, the input parameters in the Total Organic Carbon Module provide relevant information about the depositional environment, which is taken into account in the process of simulating the total organic carbon content.

In the Maturation Module, the input parameters come from geochemical analyses and Rock-Eval pyrolysis. In this case, the aim is to reconstruct from the data analyzed at each depth (or layer of the well) the conditions prior to the carbon maturation process. For this purpose, data from S1, S2, S3, maximum temperature (Tmax), vitrinite reflectance (R0) and total organic carbon measured in the rock (COTr) are used. COTr represents the amount of organic carbon contained in the rock, including soluble (bitumen) and insoluble (kerogen) organic matter. However, COTr, despite providing an indication of the amount of organic matter, does not help in the characterization of this organic matter. This characterization is much more detailed from the Rock-Eval pyrolysis data that analyzes organic matter fractions and helps to characterize the different organic compounds. Thus, data from S1, S2, S3 and maximum temperature from Rock-Eval pyrolysis can be used for this purpose to characterize organic compounds, and together with other data such as COTr provide information on, for example, the potential for generating a rock. The vitrinite reflectance and maximum temperature data can help in understanding the degree of thermal maturation of a given rock, which needs to be taken into account for the calculations of parameter reconstruction in a phase prior to the maturation process. Therefore, all these parameters are necessary for the Maturation Module simulation process.

Determination of the equations for each stage of the simulation.

Next, there is presented the determination of the equations for each step of the simulation. After entering data into the Total Organic Carbon Module, the equations for calculating the marine and terrestrial organic fractions are established in order to estimate the total organic carbon content in this simulation process. The COma and COte fractions are calculated, where the COte fraction is composed of two fractions qCO and rCO. Regarding the marine fraction (COma), the simulation process depends on the primary productivity, sedimentation rate, dry apparent density, and depending on the formulation chosen during the simulation process, it will also depend on the bathymetry. The COma simulation process in oxic environments can follow three different types of calculation methods. The marine fraction can then be calculated from multivariate equations of the type $$COma = \frac{a * PP * SR * b}{DBD},$$

such as the equation established by Müller and Suess (1979). This equation is described in the document: MÜLLER, P. J.; SUESS, E. Productivity, sedimentation rate, and sedimentary organic matter in the oceans—I. Organic carbon preservation. Deep Sea Research Part A. Oceanographic Research Papers, [S. I.], v. 26, n. 12, p. 1347-1362, 1979. There is also the possibility in the sequence of steps of the process of choosing equations that include regression of factors and processes, such as $$COma = \frac{a * CF}{DBD * SR * b},$$

such as the equation established by Stein (1986). This equation is described in the document: STEIN, Rüdiger; RULLKÖTTER, Jürgen; WELTE, Dietrich H. Accumulation of organic-carbon-rich sediments in the Late Jurassic and Cretaceous Atlantic Ocean—A synthesis. Chemical Geology, [S. I.], v. 56, n. 1, p. 1-32, 1986. And finally, there is a third possibility to estimate the fraction COma in oxic environments in the present invention. COma can also be estimated from equations that include only processes, such as $$COma = \frac{(BE * CF)}{(BE * CF + DB * SR * 10) * 100},$$

which uses the equation established by Tyson (2005) as an example. Such a formulation is described in the document: TYSON, R. V. The "Productivity Versus Preservation" Controversy: Cause, Flaws, and Resolution (Nicholas B. Harris, Org.) The Deposition of Organic-Carbon-Rich Sediments: Models, Mechanisms, and Consequences SEPM Society for Sedimentary Geology, 2005.

In the COma fraction simulation process, there are equations that use the processes of carbon flux (CF) and/or burial efficiency (BE). In this sense, a range of equations available in the simulation process established by this invention can be chosen. For the calculation of the carbon flux a possible structure is CF=a*WDb*PPc, where an example is the equation established by Antia et al. (2001), which was described in: ANTIA, Avan N. et al. Basin-wide particulate carbon flux in the Atlantic Ocean: Regional export patterns and potential for atmospheric CO2 sequestration. Global Biogeochemical Cycles, [S. I.], v. 15, n. 4, p. 845-862, 2001. However, multiple formulations for the step of CF calculation can be selected throughout the process described in this invention, including equations of this invention process. In the case of burial efficiency (BE), an example of a calculation structure is $$\log 10\left(\frac{BE}{100}\right) = \frac{a * \log 10 SR}{\log 10(SR + b)} + c,$$

where an example is the equation created by Betts and Holland (1991). This equation is described in the document: ANTIA, Avan N. et al. Basin-wide particulate carbon flux in the Atlantic Ocean: Regional export patterns and potential for atmospheric CO2 sequestration. Global Biogeochemical Cycles, [S. I.], v. 15, n. 4, p. 845-862, 2001.

The production of marine organic carbon can also be estimated for anoxic conditions, according to the following equation Coma=(PP*PF)/(DBD*SR). For this purpose, the maximum PF value must be defined during a given period time interval or depth of the analyzed well. From this, the method establishes a simple linear interpolation of the PF values over the interval, reaching the maximum PF value in the middle of the previously defined interval. Therefore, in this invention the organic carbon marine can be estimated from the combination of different methods that can be interchanged throughout the process, and also allows this estimate to be made for different depositional environments (oxic and anoxic).

The next step of the method involves simulating the production of terrestrial organic carbon (COte). The COte estimate depends on the magnitude of continental input to the well site. Thus, there is a relation between granulometry and COte content in sediments from marine environments. In this step, two terrestrial organic fractions are calculated, the terrestrial organic carbon (qCO), and the residual terrestrial organic carbon (rCO). These fractions are calculated from the sand fraction (SF) input data, and can have two types of production regimes, the high regime and the low regime, which represent the level of terrestrial organic carbon production. In both regimes, the structure for calculating the fractions is rCO=a*SF+b. In the case of the other terrestrial organic fraction, there is a conditional logic, if SF<75%, qCO=a*SF, and if SF>=75%, qCO=a*SF+b. These equations were created based on studies that intensively examined the relation of the origin, composition and diagenesis of organic matter with grain size and mineralogy. More specifically, the equations established here at this step of the process were based on the studies by Bergamaschi et al. (1997) and Keil et al. (1998). The study by Bergamaschi et al. (1997) is described in the document: BERGAMASCHI, Brian A.; TSAMAKIS, Elizabeth; KEIL, Richard G.; EGLINTON, Timothy I.; MONTLUÇON, Daniel B.; HEDGES, John I. The effect of grain size and surface area on organic matter, lignin and carbohydrate concentration, and molecular compositions in Peru Margin sediments. Geochimica et Cosmochimica Acta, [S. I.], v. 61, n. 6, p. 1247-1260, 1997. And the study by Keil et al. (1998) is found in the document: BERGAMASCHI, Brian A.; TSAMAKIS, Elizabeth; KEIL, Richard G.; EGLINTON, Timothy I.; MONTLUÇON, Daniel B.; HEDGES, John I. The effect of grains size and surface area on organic matter, lignin and carbohydrate concentration, and molecular compositions in Peru Margin sediments. Geochimica et Cosmochimica Acta, [S. I.], v. 61, no. 6, p. 1247-1260, 1997.

After entering data in the Maturation Module, the data are analyzed in relation to their quality and characterized together. As in the previous module, data is linked to the depths of samples taken from a given well. In the Maturation Module, the processes of advanced diagenesis and catagenesis are contemplated in the simulation through estimates of inert carbon (Cinerte), active carbon (Cativo), initial active Hydrogen index (IH0ativo), transformation rate (TR), total organic carbon initial (COT0), initial S2 (S20), initial Hydrogen index (IH0), and calculated vitrinite reflectance (R0). The objective of this module is to estimate these parameters from a sequence of steps in order to evaluate the amount, quality and maturation of organic carbon. The mentioned parameters are calculated from the well depth data, and S1, S2, IH, R0, COTr, and Tmax, of the samples from a given well. Thus, a sequence of logical steps is established in the simulation process to estimate the parameters of interest.

Initially, data groupings are defined following the clustering methodology using the K-near neighbors method. The objective is to select different data populations within the same database in relation to the geochemical characteristics indicated by the evaluation graphs. Such a grouping becomes necessary for the calculation of Cativo and Cinerte from data provided by COTr. This is because, in each data, grouping linear regressions are applied specifically to the COTr and S2 data, and the Cinerte is calculated from the value of the coefficient of the intersection of the line, if this coefficient is greater than zero (b>0). Otherwise, the Cativo is equal to the COTr, since the transformation rate (TR) is also equal to zero (TR=0). Therefore, for this procedure, the formulation Cativo=COTr−Cinerte is used, based on the study by Dahl et al. (2004). This equation is described in the document: DAHL, Birger; BOJESEN-KOEFOED, Jørgen; HOLM, Anders; JUSTWAN, Holger; RASMUSSEN, Egil; THOMSEN, Erik. A new approach to interpreting Rock-Eval S2 and COT data for kerogen quality assessment. Organic Geochemistry, [S. I.], v. 35, n. 11, p. 1461-1477, 2004. From the calculation of the Cativo, it is possible to calculate the IH0ativo using the equation $$IH0ativo = 100 * \frac{S2}{Cativo}$$

based on the methodology proposed by Dahl et al (2004). Subsequently, with the calculation of the IH0ativo performed, it is possible to estimate the transformation rate following the equation $$TR = \frac{IH0ativo - I}{IH},$$

which is derived from the study by Jarvie (2012). This equation is described in the document: JARVIE, Daniel M. Shale Resource Systems for Oil and Gas: Part 1—Shale-gas Resource Systems (J. A. Breyer, Org.) Shale Reservoirs—Giant Resources for the 21st Century American Association of Petroleum Geologists, 2012. However, it is also possible at this stage of the process to choose another method for calculating the TR, such as the method established by Justwan and Dahl (2005), described in: JUSTWAN, H.; DAHL, B. Quantitative hydrocarbon potential mapping and organofacies study in the Greater Balder Area, Norwegian North Sea (A. G. Dore, B. A. Vining, Org.) Petroleum Geology: North-West Europe and Global Perspectives—Proceedings of the 6th Petroleum Geology Conference Geological Society of London, 2005. If the value of TR is greater than zero, the method can proceed to the calculation of the initial total organic carbon, using the equation $$COT0 = COTr + \left[S2 * \frac{Tr}{1 - Tr}\right] * \alpha,$$

based on the methodology established by Justwan and Dahl (2005). It is also possible at this step of the process to simulate the value of initial S2 from $$S20 = \frac{S2}{1 - Tr},$$

also following the method of Justwan and Dahl (2005). After estimating the S20, it is possible to proceed to the next step of the process and calculate the initial Hydrogen index using the equation $$IH0 = \frac{S20}{COT0},$$

based on the study by Dahl et al. (2004). Additionally, at the end of the process, it is possible to obtain the calculated vitrinite reflectance (R0), using R0=(a*Tmax)−b, based on the equation proposed by Tissot and Welte (1984). This equation is described in the document: TISSOT, Bernard P.; WELTE, Dietrich H. Diagenesis, Catagenesis and Metagenesis of Organic Matter BT—Petroleum Formation and Occurrence. In: TISSOT, Bernard P.; WELTE, Dietrich H. (org.). Berlin, Heidelberg: Springer Berlin Heidelberg, 1984, p. 69-73.

After selecting the equations in the modules that make up the sequence of logical steps established by the method of this invention, it becomes possible to estimate the amount and quality of organic carbon for a given well (one-dimensional), focusing on source rocks in environments marine.

Prediction of the Amount of Total Organic Carbon (Total Organic Carbon Module).

The prediction of the amount of total organic carbon (Total Organic Carbon Module) is carried out from the choice of the equations of the previous step.

The method establishes that the simulation can proceed to the next steps, in which estimates of amount and quality of organic carbon are provided. The Total Organic Carbon (COT) content is provided by the Total Organic Carbon Module. The final COT content is the result of the sum of the marine (COma) and terrestrial (COte) fractions, the latter being composed of two subfractions (qCO and rCO). Therefore, COT=COma+COte. The results of the calculations of these organic fractions may differ in terms of sample resolution, depending on the resolution of the input data provided. Therefore, the simulation process of this invention deals with these resolution differences by determining a value for final interpolation of the calculated TOC data. The resolution value for the interpolation is established in meters and is related to the well depth interval. The results obtained can be exported at the end of this COT quantification process.

Prediction of Total Organic Carbon Quality (Total Organic Carbon Module).

At this step, after the marine and terrestrial organic fractions have been quantified, it is possible to proceed with the simulation process and generate quality estimates of the organic matter still in the Total Organic Carbon Module. This is because from the quantifications of each organic fraction (COma, qCO and rCO), it becomes possible to apply a three-source mixture model to estimate values of Hydrogen Index (IH), Oxygen Index (IO) and isotopic signature of carbon (δ13C). To this end, reference values are defined for each fraction, and these values are multiplied by the amounts of each fraction, so that a final average value is estimated for each of the parameters mentioned above for each layer of the well. For example, IO=IOCOma*COma+IOqCO*qCO+IOrCO*rCO, where IO is the calculated oxygen index for a given layer, IOCOma is the reference oxygen index value for marine organic carbon, COma is the amount of marine organic carbon that was previously calculated, IOqCO is the oxygen index reference value for terrestrial organic carbon, qCO is the amount of terrestrial organic carbon that was previously calculated, IOrCO is the oxygen index reference value for residual terrestrial organic carbon, and rCO is the amount of residual terrestrial organic carbon that was previously calculated. The simulation process uses reference values for each fraction based on organic matter characterization studies, but the values can be modified during the processing of this step. The results obtained can be exported at the end of this process. With the results obtained in this step, it is possible to use a classification of organic facies based on the obtained values of COT, IH and IO. For example, the classification established by Jones (1987). This classification is described in: JONES, R. W. Organic Facies, in: Brooks, J., Welte, D. (Eds.), Advances in Petroleum Geochemistry. Academic Press, London, 1987, p. 78-80.

Quality Prediction and Evaluation of Organic Carbon Maturation Processes (Maturation Module).

In this step, all the necessary parameters are calculated to evaluate the quality of the organic carbon and how it was influenced by the processes related to the maturation of the organic matter. Therefore, the results of inert carbon (Cinerte), active carbon (Cativo), initial active Hydrogen index (IH0ativo), transformation rate (TR), initial total organic carbon (COT0), initial S2 (S20), initial Hydrogen index (IH0), and calculated vitrinite reflectance (R0). With these results, it is possible to evaluate the state in which the organic carbon was found before being subjected to the diagenetic and thermal maturation processes. The results obtained can be exported at the end of this process. At this step, it is also possible to use a classification of organic facies based on the values obtained from COT0 and IH0, following the classification of Jones (1987).

EXAMPLES

Total Organic Carbon Simulation Process.

The process of simulating the content of organic matter mediated by the invention was tested and validated from data measured in sediments explored in the sedimentary basin of Espirito Santo, southeastern Brazilian shore. The tectonic-stratigraphic evolution of this basin is usually divided into three main super-sequences, (i) rift sequence (Valangian to Aptian, ~135-125 Myr), post-rift or transitional sequence (middle Aptian to early Albian, ~120-110 Myr) and drift sequence (medium Albian to Recent, ~110 Myr). Throughout the entire Late Cretaceous to the Paleogene (~100-23 Myr), a second order transgressive tendency prevailed and thick sequences of marine muds (marls and shales) were deposited especially in the most distal part of the basin composing the so-called Urucutuca formation. It is on these marine sequences that the application examples described in this section focus.

The modeling begins with the process of simulating the organic carbon content (FIG. 1) in the size of an exploratory well in the Espirito Santo basin called ES-1. Currently, this well is at a water depth of 1841 m and its geophysical and geochemical data make up an interval between 1880.6 and 5405.7 m in depth in the sediment with estimated ages between ~60 and 100 Myr. To run the simulation, the following data are used, namely:

1—Depth and age model [millions of years, Myr]-chronostratigraphic information of any nature that provide temporal estimates for the well layers;
2—Sedimentation rate [SR-cm/ka]—rate at which particles dispersed in the water column decant towards the sediment, filling a given accommodation space in a given period of time;
3—Primary productivity [PP-gC/m$^2$/year]—rate corresponding to the fixation of organic carbon by autotrophic organisms in the photic zone of the oceans;
4—Dry apparent density [DBD-g/cm$^3$]—physical property linked to the granulometric characteristics of the different classes of sediments;
5—Bathymetry/paleobathymetry [WD-m]—depth of the water depth where a certain sedimentary layer was found in the past;
6—Area fraction [SF-%]—contribution of detrital material used by the process to estimate carbon originating from the continent and not produced by marine biomass.

After introducing this collection of data, the process proceeds to a step in which the variables can be adjusted so that the invention correctly assigns the source of the respective data in the inserted files. If, eventually, some of the previously listed data cannot be introduced into the invention, the process as a whole can still be executed, since it is possible to assign previously known constant values to each of the input variables.

Having the invention correctly understood the information contained in the input data or otherwise designated as constants, the process proceeds to the step of equating the total organic carbon contained in the stratigraphic/chronological interval of interest. At this stage, the process begins by choosing the marine organic carbon equation that best fits the nature of the provided data. There are currently three configurations available in the invention for calculating marine organic carbon (COma). These formulations can be described from multivariate equations of the type $$COma = \frac{a*PP*SR*b}{DBD} \text{ or } COma = \frac{a*CF}{DBD*SR*b},$$

that include factor and process regression, or from equations that include only processes, such as $$COma = \frac{(BE*CF)}{(BE*CF+*SR*10)*100}.$$

In this application example, there is demonstrated the estimated total organic carbon from the three formulations described. In general, these equations combine a given rate of organic carbon production by the biota in a given interval of time and space with a rate of removal of this carbon towards the ocean floor. When the last two equations are selected for the process of calculating the total organic carbon within the invention, it is also necessary to define two other equations referring to the estimation of the carbon flux (CF) and burial efficiency (BE). For the carbon flux, the invention contains six available solutions in which the biological production exported to the seabed varies as a function of the depth of the water column in the chronological interval of interest. As for the burial efficiency, the invention has two equations in its structure that work according to the total rate of sediments that flow towards the ocean floor and that act by removing the organic particles of interest from the water column. In this application example, there were selected an equation of the type CF=a*WDb*PPc to estimate the flux of organic carbon and an equation of the type $$\log 10\left(\frac{BE}{100}\right) = \frac{a * \log 10SR}{\log 10(SR + b)} + c$$

for estimation of carbon burial efficiency.

With the equations for calculating the marine organic carbon selected, the process also requires the determination of the input of terrestrial organic carbon (COte) calculated by an equation of the type COte=rCO+qCO, which was selected in its "high" operating regime. From the selection of all processes necessary for the desired estimates, the invention performs the calculations and graphically displays the individual result of measurements of marine (COma), terrestrial (COte) and total (COT) organic carbon. The final results, together with the settings established during the process, can be exported in ".txt" or ".csv" format so that, eventually, they can be worked on external applications to invention.

FIG. 3 compares the results of the simulation process of the total organic carbon content of the invention (COT) with the measured total organic carbon (COTr) from samples from exploratory well ES-1. The simulation by the invention indicates three main intervals of high organic carbon deposition: between ~5000 and 4500 m, ~3500 and 3000 m and ~3000 and 2800 m deep in the sediment. Note that the intervals between ~5000 and 4500 m and ~3000 and 2800 m are consistent with elevations of total organic carbon measured in the rocks of well ES-1 (FIG. 3). That is, the invention correctly indicates the presence of intervals with a high carbon content that could represent exploratory success in prospecting for oil or gas. In the case of well ES-1, the interval contained between ~5000 and 4500 m contains two anoxic events from the late Cretaceous and, therefore, the indication of higher total organic carbon contents by the invention in this depth range is relevant, since these events were characterized by a strong deposition of organic carbon in the global oceans. As for the interval between ~3500 and 3000 m, the same elevation is not seen in the organic carbon content in the rocks of well ES-1. It is worth to emphasize that the direct comparison of the simulation of total organic carbon performed by the invention with the organic content of the exploratory well is not the most indicated way to estimate the success of the simulation, since the processes related to the maturation of the organic matter in the rocks of the well over geological time altered the initial composition of the deposited organic carbon. That is, the invention in this module simulates the total organic carbon initially sedimented in the depositional environment; however, it is necessary to consider that the diagenetic and catagenetic processes inside the sediments change this initial composition, as will be demonstrated in the next section. For this reason, the process performed by the invention tends to reconstruct relatively larger values than those measured in the well rocks. Despite these limitations, this comparison allows at least an initial evaluation of the success of the process.

After simulating the total organic carbon content, the invention makes it possible to evaluate the quality of the simulated organic matter during the previously described process. For this, it is necessary to provide the invention with reference values associated with the Hydrogen Index (mg HC/g COT), Oxygen Index (mg CO2/g COT) and isotopic ratio (δ13C) of marine organic carbon (COma) and the kerogen (qCO) and residual (rCO) fractions of terrestrial organic carbon. In this application example, the quality of the organic matter is estimated with the simulation results of the first equation used to calculate the total organic carbon. FIG. 4 illustrates the process of simulating the quality of organic matter estimated by the invention for well ES-1.

Organic Matter Maturation Simulation Process

The organic matter maturation simulation process was tested in the ES-1 exploratory well shown above. The evaluation of maturation by the invention seeks to determine the chemical changes in the sedimentary organic matter due to the increase in temperature due to the advance of burial. This maturation can occur in three stages: diagenesis, catagenesis and methanogenesis. The maturation process implemented by the invention allows characterizing the source rock based on evaluations regarding the amount of total organic carbon (poor, moderate, good and very good), type of kerogen (I, II, III and IV) and maturation stage (recent, generation peak, late and post-mature). In an innovative way, the invention also carries in its processes the Relative Hydrocarbon Potential (RHP) that characterizes oxygenation conditions and redox potential of the source rock.

For the execution of the simulation of maturation of organic matter in the exploratory well ES-1, the following data measured in the laboratory need to be used in the environment of the invention, namely:

1—Total Organic Carbon of the rock [COTr %];
2—S1 [mg HC/g rock];
3—S2 [mg HC/g rock];
4—Hydrogen Index [IH—mg HC/g COT];
5—Oxygen Index [IO—mg CO2/g COT];
6—Vitrinite reflectance [Ro—%];
7—Maximum temperature [Tmax—° C.]

These data will allow the invention to return the following parameters, namely:

1—Active Carbon [Cativo-%];
2—Inert Carbon [Cinerte-%];
3—Transformation Rate [TR];
4—Initial total organic carbon value [COT0-%];
5—Value of the initial active Hydrogen index [IH0ativo-mg HC/g COT];
6—Initial S2 value [S20-*mg* HC/g rock];
7—Calculated vitrinite reflectance—[Calculated R0-%].

Similar to the previous total organic carbon simulation module, the process proceeds to a step in which the variables can be adjusted so that the invention correctly assigns the source of the respective data in the inserted file (FIG. 2). It is also possible to determine a previously known constant value for any of the variables. Active carbon (Cativo) is the portion of total organic carbon that can still be transformed by maturation processes to generate oil or gas. This parameter is calculated by the invention with an equation of the type Cativo=COTr−Cinerte. On the other hand, the portion referring to inert carbon (Cinerte) is that already transformed and, therefore, does not have generating potential. The transformation rate (TR) is the ratio between the oil generated by the kerogen and the total amount of oil that the initial kerogen was able to generate and is estimated by the invention from the indexes of active initial hydrogen (IH0ativo) and the Hydrogen index (IH) corresponding to the amount of pyrolyzable organic compounds in an equation of the type $$TR = \frac{IH0ativo - IH}{IHativo}.$$

The initial total organic carbon (COT0) refers to the deposited carbon that has already gone through the initial stages of diagenesis, being estimated with an equation of the type $$COT0 = COTr + \left[S2\frac{Tr}{1 - Tr}\right] * a.$$

The Hydrogen index of this initial total organic carbon is the initial Hydrogen index (IH0) of the sample, being solved by the invention by an equation of the type $$IH0 = \frac{S20}{COT0}.$$

S2 is the peak in the Rock Eval gradual heating diagram that represents the generation of hydrocarbons by the cracking of the kerogen in the sample, with the initial S2 value being the peak value after primary diagenesis.

In the invention, this variable is solved by the equation of type $$S20 = \frac{S2}{1 - Tr}.$$

Finally, the invention estimates the index relative to the vitrinite reflectance (R0) of the sample after primary diagenesis. This is an important classification petrographic index of thermal maturation that is calculated from the maximum temperature in an equation of the type R0=(a*Tmax)−b.

Advantageously, the invention enables a series of previous evaluations based on the correlation between the initially introduced data. FIGS. 5 and 6 illustrate how the invention classified the rocks from exploratory well ES-1 according to their generation potential. With regard to S2 and the total organic carbon of the rocks, the invention indicates that the well has an “Excellent” to “Good” potential near the base that tends to decay to “Poor” in the upper sections (FIGS. 5A and 5B). For the Hydrogen index, the invention distributes most of the well samples between the “Gas” and “Gas+Oil” windows (FIG. 5C). The maximum temperature values indicate that only the depths below 4500 m reached values high enough to enter the “Oil Window” (FIG. 6A), similar to that demonstrated by the reflectance of the vitrinite (FIG. 6B). Due to the correlation between the total organic carbon in the rocks and S2, the invention classified most of the exploratory well ES-1 as “Poor” in terms of generation potential (FIG. 6C). The invention, therefore, provides dynamism and practicality to the initial process of interpretation of the geochemical parameters usually used in the industry. The process then proceeds to calculate the active carbon (Cativo) considering how the data were grouped into clusters based on the previous correlation between total organic carbon and the S2 of the rocks. With the clustering defined, the invention estimates each of the seven output variables previously listed based on their descriptive equations (FIG. 7A-G). The initial total organic carbon (COT0) estimated at this step by the invention indicates what was the organic carbon content of the rocks before it underwent catagenesis and methanogenesis processes during burial. When comparing this information with the total organic carbon simulations demonstrated in the previous topic, there can be seen that the total organic carbon simulations are much more adherent, especially in the depth interval between ~3500 and 3000 m (FIG. 8). In fact, a large increase in the contribution of organic carbon exists in this range; however, the processes of maturity over geological time ended up consuming the same. By compensating for these effects, however, this accumulation of organic carbon is revealed indicating that the invention previously predicted it satisfactorily (FIGS. 3 and 8).

FIG. 9 emphasizes how the combination between the simulation processes of total organic carbon and maturation of organic matter were, in general, successful. In this figure, in addition to the previously developed total organic carbon simulations, the total organic carbon calculated using a preservation factor of 25% associated with anoxia conditions was also incorporated. In this context, the simulated total organic carbon showed a relevant adherence both with the organic carbon measured in the rock (COTr) and with the initial organic carbon estimated after the maturation process (COT0). This indicates that, within the chronostratigraphic windows referring to events of this nature, it is necessary to consider a certain preservation factor in order to achieve a more successful simulation. Once outside the limits of the anoxic event, simulations of total organic carbon without considering a preservation factor have a better correspondence with organic carbon after compensating for the effects of maturation (FIG. 9).

FIG. 9 emphasizes how the combination between the simulation processes of total organic carbon and maturation of organic matter were, in general, successful. In this figure, in addition to the previously developed total organic carbon simulations, the total organic carbon calculated using a preservation factor of 25% associated with anoxia conditions was also incorporated. In this context, the simulated total organic carbon showed a relevant adherence both with the organic carbon measured in the rock (COTr) and with the initial organic carbon estimated after the maturation process (COT0). This indicates that, within the chronostratigraphic windows referring to events of this nature, it is necessary to consider a certain preservation factor in order to achieve a more successful simulation. Once outside the limits of the anoxic event, simulations of total organic carbon without considering a preservation factor have a better correspondence with organic carbon after compensating for the effects of maturation (FIG. 9).

In general, the combination between the two simulation processes performed in the modules of the invention indicates that the rocks of the exploratory well ES-1 have few windows with significant potential for hydrocarbon generation, which may result in financial losses if steps forward of exploitation were put into practice. Therefore, the results generated by the invention would suggest to industrial decision-making processes that more investment capital should not be allocated to well ES-1.

The invention claimed is:

1. A method for determining a content, quality and maturation of organic matter in a marine environment for exploration of oil wells, the method comprises:

i) performing (multi) one dimensional one-dimensional or multi-dimensional simulation of the content and quality of total organic carbon in marine sedimentary basins along a chronostratigraphic profile of an exploratory well;

ii) grouping environmental variables in a structure of biological matter production equations in the marine environment, transport rates, decay towards ocean floor and efficiency with which it is buried;

iii) determining a terrestrial organic carbon (COte) transfer regime for a marine site under analysis, in which terrestrial fractions referring to kerogen (qCO) and residual carbon (rCO) are estimated from sand fraction (SF), where therCO is calculated from an equation of rCO=a*SF+b in which a and b are constants and the qCO comes from a conditional logic where if SF<75%, qCO=a*SF, and if SF>=75%, qCO=a*SF+b;

iv) designating a preservation factor (PF) associated with generation of an anoxia interval at the site under analysis, which enhances conservation of the organic matter along its depositional route;

v) defining a quality of organic matter from a three-source mixture model;

vi) calculating values of hydrogen index, oxygen index and carbon isotopic signature along the profile of the exploratory well;

vii) performing one-dimensional or multi-dimensional simulation of maturity of organic matter in sedimentary basins and categorizing this matter into indices of amount, quality and maturity, and evaluating advanced diagenesis and catagenesis processes to determine a generator potential of oil and/or natural gas;

viii) selecting laboratory tests that provide starting estimates for the maturity process of the organic matter;

ix) evaluating characteristics of the organic matter related to its amount, quality, stage of thermal maturation and relative potential to generate hydrocarbons;

x) grouping data referring to the total organic carbon and a peak in a Rock Eval gradual heating diagram that represents generation of hydrocarbons by cracking of kerogen in the sample (S2) for determination of active and inert fractions of the total organic carbon to determine geochemical parameters of maturation of the organic matter to expand oil exploration to deep marine environment.

2. The method of claim 1, further comprising determining production of marine organic carbon (COma) and transfer of terrestrial organic carbon (COte) with a finite number of equations and their possible recombinations in each geological layer of the profile of the exploratory well.

3. The method of claim 1, further comprising determining a degree of degradation of organic matter along its depositional path by designating a preservation factor (PF) associated with an anoxia zone defined by $$PF = \frac{OCAR}{PP},$$

where OCAR is a rate of accumulation of organic carbon estimated with an equation of OCAR=COma*DBD*SR, in which case, COma=(PP*PF)/(DBD*SR), wherein PP is primary productivity, DBD is a dry apparent density, and SR is sedimentation rate.

4. The method of claim 1, wherein the three-source mixture model evaluates quality of organic matter after simulating total organic carbon, and which is applied from border values of a Hydrogen index, Oxygen index and δ13C, according to the equation IH=IHCOma*[COma]+IHqCO*[qCO]+IHrCO*[rCO].

5. The method of claim 1, further comprising classifying the organic matter in relation to its amount, type of kerogen and maturation level based on a correlation between S2 and total organic carbon (COT vs. S2), Hydrogen index and Oxygen index (IH vs. IO), maximum temperature and vitrinite reflectance (Tmax vs. R0).

6. The method of claim 1, wherein the total organic carbon measured in the rock (COTr) and S2 are organized in groupings, and a linear regression y=ax+b that determines an intercept value of the straight line (b) to calculate the total active organic carbon (Cativo) and the total inert organic carbon (Cinerte), where, if b #0 the active organic carbon is calculated with an equation of Cativo=COTr−Cinerte.

7. The method of claim 6, wherein a Hydrogen index (IH0ativo) of an active fraction of active organic carbon (Cativo) is defined by an equation of $$IH0ativo = 100 * \frac{S2}{Cativo}.$$

8. The method of claim 7, wherein a transformation rate (TR) is determined once the IH0ativo is found by an equation of $$TR = \frac{IH0ativo - 1}{IH}.$$

9. The method of claim 8, wherein an initial total organic carbon (COT0), after initial stages of diagenesis, is estimated after determining the transformation rate in an equation of $$COT0 = COTr + \left[S2 * \frac{Tr}{1 - Tr}\right] * a,$$

where α is a constant.

10. The method of claim 8, wherein the initial S2 of the sample ($S2_0$), after primary diagenesis, is measured by an equation of $$S20 = \left[\frac{S2}{1 - Tr}\right].$$

11. The method of claim 10, wherein the initial Hydrogen index (IH0) associated with the initial total organic carbon (COT0) is measured through an equation of $$IH0 = \frac{S20}{COT0}.$$

12. The method of claim 1, wherein a vitrinite reflectance calculated in the sample, after the primary diagenesis, is determined from an equation of R0=(a*Tmax)−b, in which a and b are constants and Tmax is the maximum temperature.

* * * * *